US 7,303,705 B2

(12) United States Patent
Panton, Jr.

(10) Patent No.: US 7,303,705 B2
(45) Date of Patent: Dec. 4, 2007

(54) THERMOPLASTIC SPINE BOARD WITH ERGONOMIC FEATURES

(76) Inventor: George S. Panton, Jr., 8120 S. A1A Hwy., Melbourne Beach, FL (US) 32951

( * ) Notice: Subject to any disclaimer, the term of this patent is extended or adjusted under 35 U.S.C. 154(b) by 0 days.

(21) Appl. No.: 10/616,978

(22) Filed: Jul. 11, 2003

(65) Prior Publication Data

US 2004/0060115 A1 Apr. 1, 2004

Related U.S. Application Data

(60) Provisional application No. 60/395,333, filed on Jul. 12, 2002.

(51) Int. Cl.
*A61B 19/00* (2006.01)
(52) U.S. Cl. .................. 264/46.5; 5/628; 264/46.6; 264/46.4; 264/545
(58) Field of Classification Search ............ 5/625–628; 128/870; 441/129, 83, 63; 264/46.4, 267, 264/328.1–328.2, 465, 263, 545, 46.5, 46.6
See application file for complete search history.

(56) References Cited

U.S. PATENT DOCUMENTS

| | | | |
|---|---|---|---|
| 4,033,000 A | 7/1977 | Bonifay | |
| 4,183,110 A | 1/1980 | Kidd et al. | |
| 4,668,567 A | 5/1987 | Williams | |
| 5,190,056 A | 3/1993 | Hull | |
| 5,274,864 A | 1/1994 | Morgan | |
| 5,360,393 A | 11/1994 | Garth et al. | |
| 5,473,784 A * | 12/1995 | Nixon et al. .................. 5/625 |
| 5,507,044 A * | 4/1996 | Williamson et al. ..... 5/81.1 RP |
| 5,749,374 A | 5/1998 | Schneider, Sr. | |
| 5,950,627 A * | 9/1999 | Bologovsky et al. ....... 128/869 |
| 6,061,853 A * | 5/2000 | Laaksonen et al. ............ 5/625 |
| 6,065,165 A | 5/2000 | Delk et al. | |
| 6,073,287 A | 6/2000 | Svenson | |
| 6,352,460 B1 | 3/2002 | Eiband et al. | |
| 6,715,170 B2 * | 4/2004 | Richmond ..................... 5/625 |

FOREIGN PATENT DOCUMENTS

| | | |
|---|---|---|
| GB | 840394 A | 7/1960 |
| GB | 2 143138 A | 2/1985 |
| GB | 2182570 A | 5/1987 |

OTHER PUBLICATIONS

DynaMed Emergency Services Products Fall/Winter 2001 Catalog.
Laerdal 2001 Lifesaving Products Catalog, pp. 124-126.
Ferno Millennia Backboard Users' Manual, Jul. 1998.
MDS Matrx Catalog 2001.
PCT International Search Report for PCT/US03/21837 mailed on Nov. 12, 2003.
European Search Report for Application No. 03 764 571.0 mailed on Feb. 16, 2006.

* cited by examiner

*Primary Examiner*—Patricia Engle
*Assistant Examiner*—Fredrick Conley
(74) *Attorney, Agent, or Firm*—Rader Fishman & Grauer PLLC; Ronald P. Kananen

(57) ABSTRACT

An apparatus and method are disclosed for providing a foam-filled thermoplastic spine board. An upper surface of the spine board has a cradle configuration to assist in more comfortably positioning a patient. The spine board includes hand holds for transporting the patient. Being free from metallic parts, the spine board is X-ray translucent and/or radio translucent.

24 Claims, 5 Drawing Sheets

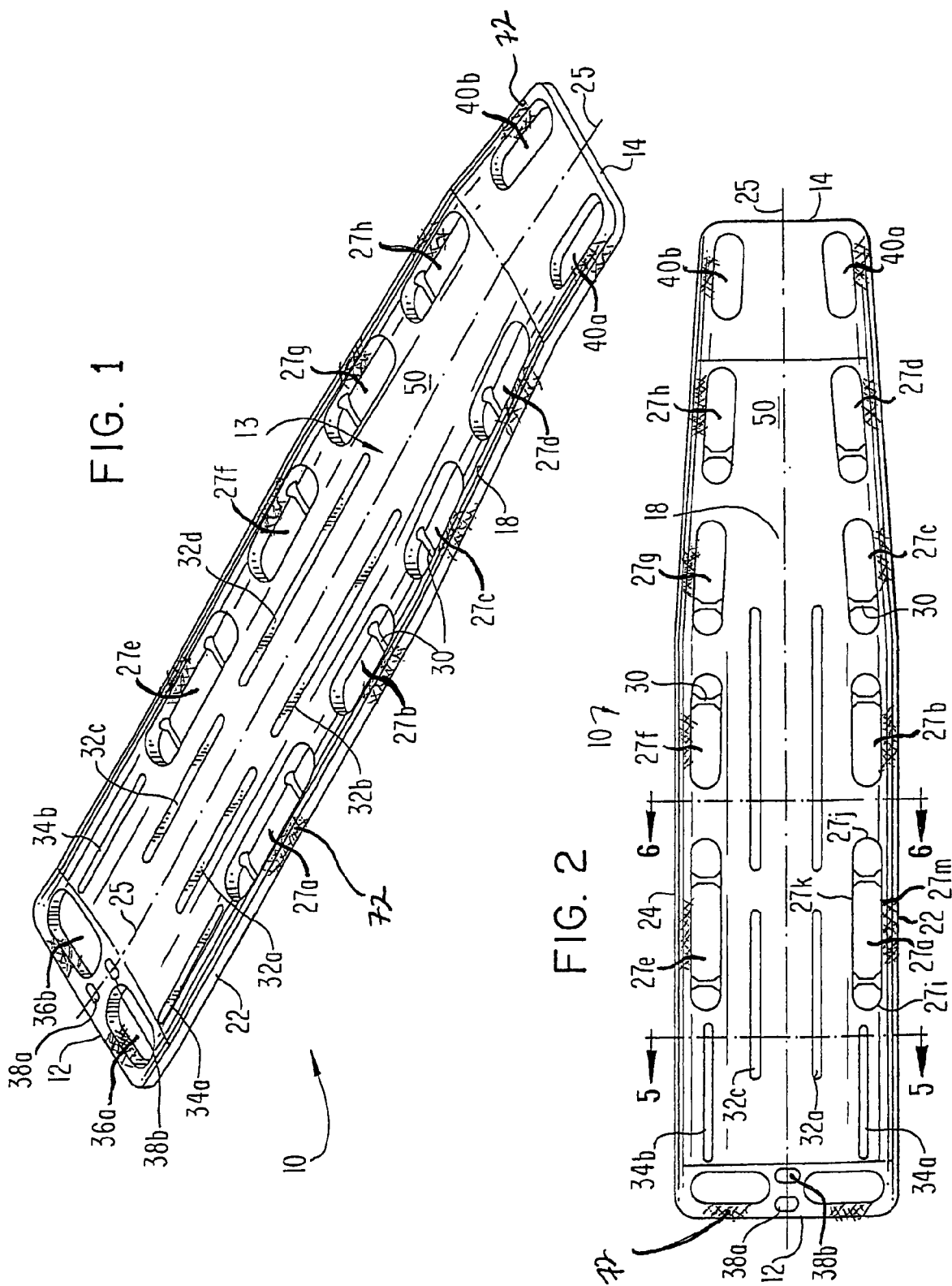

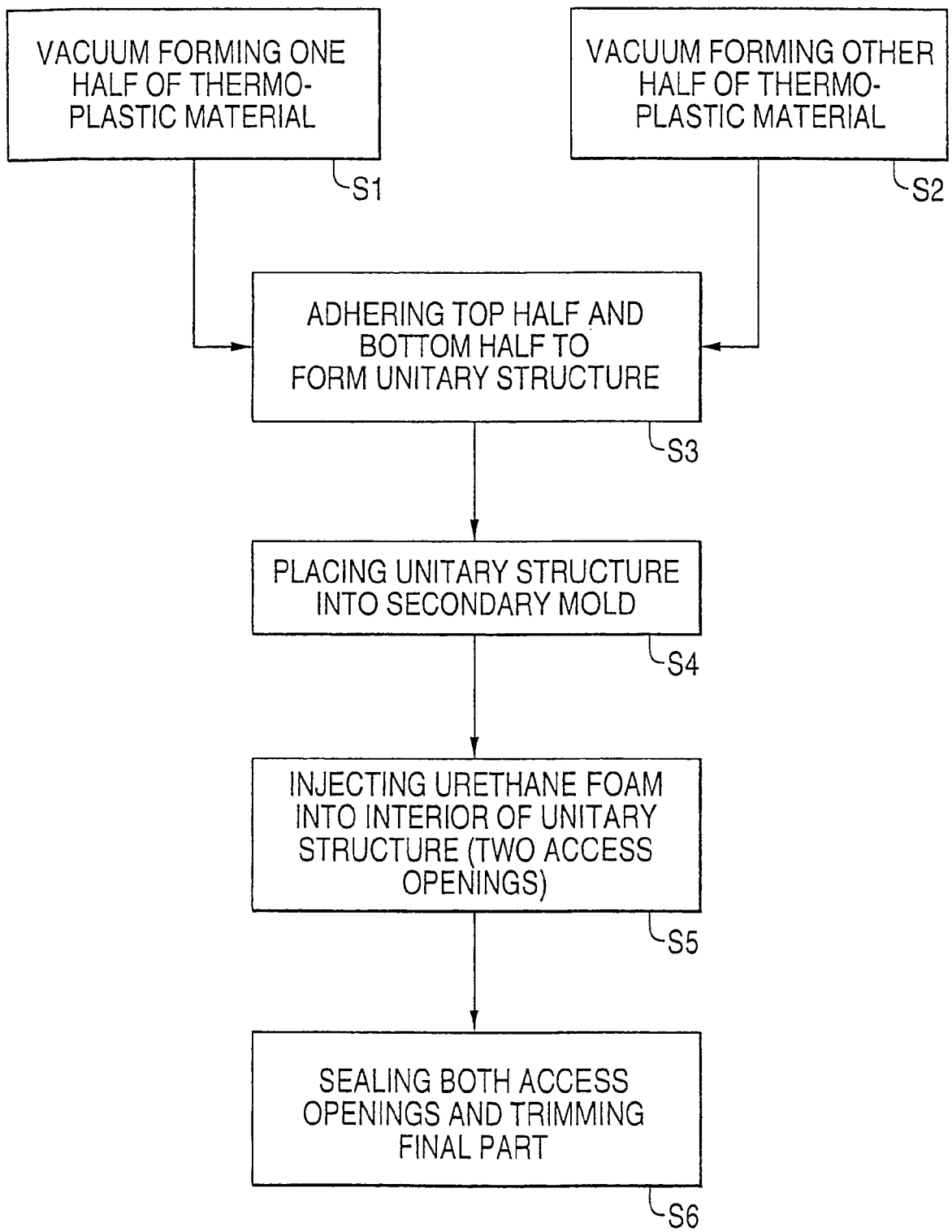

THERMOPLASTIC SPINE BOARD WITH ERGONOMIC FEATURES

This application claims the benefit of Provisional Application No. 60/395,333 filed Jul. 12, 2002.

BACKGROUND OF THE INVENTION

1. Field of the Invention

This invention relates generally to spine boards used for carrying persons usually in emergency situations. More particularly, this invention relates to a light-weight, foam-filled, thermoplastic spine board with a number of features attractive to firefighters, emergency medical service (EMS) personnel, lifeguards, and the like. Still more particularly, this invention relates to such a spine board, sometimes referred to as a back board, with a plurality of features and a method for making the same.

2. Brief Description of the Prior Art

A number of stretcher-like structures are known in the art for transporting persons in distress caused by trauma, injuries, catastrophic illness, or the like. In such emergency situations, the time between the situation and diagnosis and/or treatment is essential. Therefore, it is a concern for such patient-transporting structures to attend to minute detail with an eye toward saving time.

Known are back boards having a patient portion, or spine boards, with a variety of carriers for manually grasping hand holds for the spine boards and transporting the patient from an emergency site to a rescue vehicle, for example. One such type of spine board, with a plurality of hand holds and a neck restraining device, usually referred to as a head immobilizer, is shown in U.S. Pat. No. 5,630,393. A feature for newly-emerging improved spine boards that would be desirable is an ability to adapt existing head immobilizers currently known to the market.

Some spine boards known to the art are made of wood. However, those boards are sometimes not satisfactory because of their tendency to chip and splinter in rough handling, thus increasing the possibility for further injury to a patient. More importantly, with the rise in a risk of serious infectious disease from the unintended transfer of body fluids from one patient to another, wood is losing its favor as product suitable for manufacture. Wood, in its worst scenario, can become a carrier for such infectious pathogens from a first patient to a second patient using the same carrier without any knowledge or awareness for the second patient.

Efforts to make such spine boards from plastic have not been totally successful because of a need for lateral and longitudinal strength to handle heavy patients, perhaps up to about 600 pounds. In addition, provision must be made in such plastic spine boards to insure buoyancy. In general, the interior of such plastic spine boards is not filled, to preserve buoyancy.

An apparent known method of making such a plastic spine board includes a step of making individual parts of plastic and assembling such parts. This method is labor intensive and costly, while risking inadvertent disassembly during emergency usage. Another apparent known method includes a step of molding a plastic in a suitable shape to form a board-like structure. But no effort is made to insure structural integrity, buoyancy, and an absence of infectious growth sites.

Thus, it is an overall object of this invention to provide an improved spine board with a number of ergonomic features attractive to firefighters, emergency medical service (EMS) providers, and others, such as are explained further in this disclosure. Moreover, a method of making such a spine board is also disclosed.

BRIEF SUMMARY OF THE INVENTION

It is an overall object of this invention to provide a thermoplastic spine board that has ergonomic features addressing current need of emergency personnel in this art.

It is another overall object of this invention to provide a formed thermoplastic spine board that is filled with foam to inhibit infectious growth sites.

It is another general object of this invention to provide a method for making a vacuum-formed, foam-filled, thermoplastic spine board that is unitary and integral.

Directed to achieving these and other general objects, and addressing ergonomic needs in the art, the invention relates generally to a spine board having a sealed unitary board structure defining a board structurally adapted to transport a patient and having at least two pair of hand holds. The unitary board structure is hollow. The unitary board structure is made from opposed, mating top and bottom portions, or halves, secured to each other by thermoplastic welding to define the board. This thermoplastic welding includes thermo-welding or pressure thermo-welding. The interior side of each panel is corrugated or rough textured in such a manner that when foam is injected into the finished part, the bond of the foam to the plastic interlocks to minimize delamination. Foam completely fills the interior of the board and bonds exceptionally well to the corrugated or rough textured interior shell.

Preferably, the board contains a plurality of submersion-assisting slots to assist in submerging the board during aquatic rescues. The board further includes a plurality of side hand holds having pins molded therein for receiving quick-connecting clips. The pins are preferably barbell-shaped to center the clips at a center of the pin. A bottom surface of the board defines ribs extended therefrom to provide a rest for the board when placed on a surface. The tail end of the board is preferably downwardly tapered. The ribs thus extend downwardly at least as much as the distal end of the downwardly-extending portion lies beneath a plane of the bottom surface of the board.

The board is characterized as being free from metallic parts, so that the board is X-ray translucent and/or radio translucent. Preferably an upper surface of the board has a cradle configuration to assist in more comfortably positioning a patient.

A second aspect of the invention relates to a method for making a spine board according to the invention. A first step of forming, such as by vacuum forming a thermoplastic material, opposing, mating board portions together defining the board. Next, the opposed mating portions are thermo-welded or pressure thermo-welded to one another to form a hollow unitary board structure. A step of injecting foam, such as urethane foam, into an interior of the unitary board structure, follows, through an ingress opening, while allowing for egress of air from he interior to assure complete filling of the structure. The injected foam is preferably urethane foam. The structure is then sealed. The method further includes a step, prior to injecting the foam, of securing the thermo-welded or pressure thermo-welded unitary board structure within a secondary mold.

These and other features of the invention, in each of its aspects, will become apparent from a detailed review of the written description of the invention and the accompanying drawings.

BRIEF DESCRIPTION OF THE DRAWINGS

In the drawings:

FIG. 1 is a top, perspective view of the spine board according to an embodiment of the invention.

FIG. 2 is a top, plan view of the spine board according to an embodiment of the invention.

FIG. 8 is a simplified block diagram of the method of making the spine board according to an embodiment of the invention.

Throughout the drawing figures, like reference numerals will be understood to refer to like parts and components.

DETAILED DESCRIPTION OF THE PREFERRED EMBODIMENT

Figure 3:
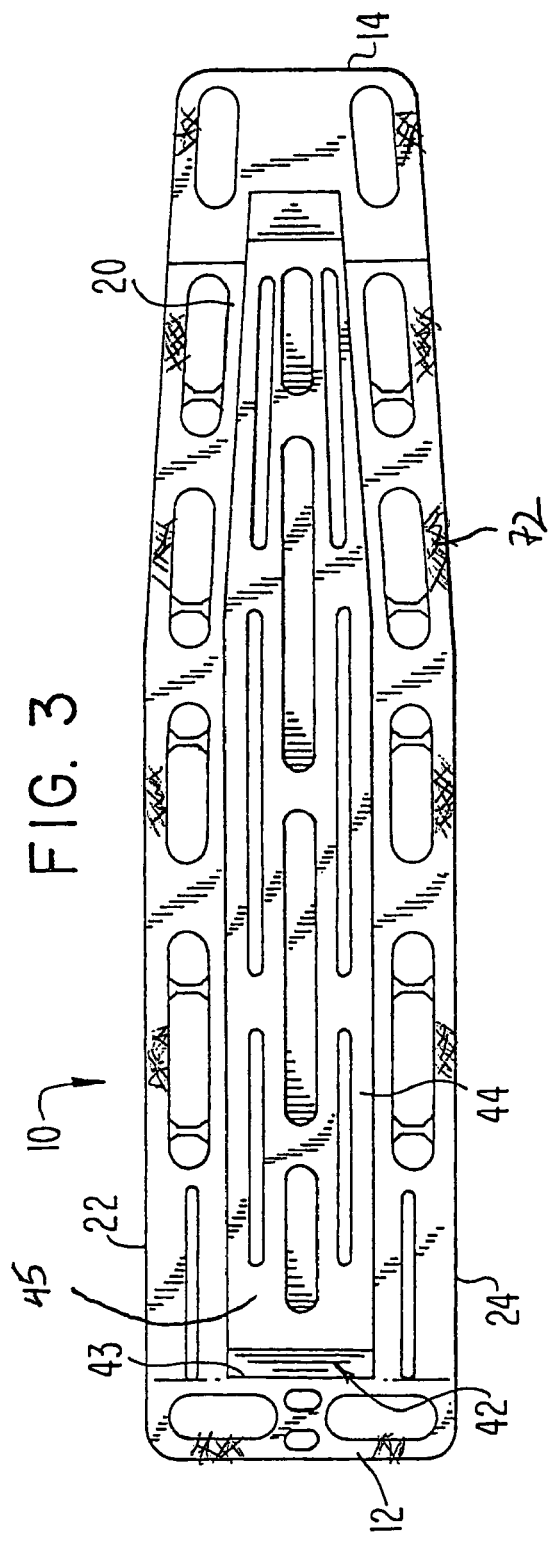
FIG. 3 is a bottom plan view of the spine board according to an embodiment of the invention.

FIGS. 1 to 7 illustrate an embodiment of a lightweight, vacuum-formed thermoplastic spine board 10, according to the invention, having a head end 12, a main body portion 13, and a tail end 14. The tail end 14 is narrower than the head end 12, so the body portion 13 narrows accordingly. The spine board 10, when completed, is a unitary, sealed structure that has a foam core 16 (shown at least within the cross sectional views of FIGS. 5A, 5B, 6A and 6B).

The spine board 10 may be made from a thermoplastic material, such as an ABS resin or other suitable thermoplastic material, with a foam core 16 made from a polyethylene, or urethane foam core. The spine board 10 is further defined by a top surface 18 (best seen in FIGS. 1, 2 and 4), a bottom surface 20 (best seen in FIGS. 3 and 4), a right side portion 22 interconnecting the top and bottom surfaces 18, 20, and a left side surface 24 interconnecting the top and bottom surfaces 18, 20. For a convenient convention, the terms "right side portion" and "left side portion" shall refer to the side portions of the spine board 10 when viewed from the head end 12 toward the tail end 14 from above the board 10.

As will be explained in connection with FIG. 8, the board is preferably vacuum-formed. That is, a top half or portion 17 and a bottom portion 19 (best seen in FIG. 7) are formed in a top portion die and a bottom portion die to make the mating portions 17, 19 secured together along a parting line 15 during manufacture to form a unitary, outer, hollow thermoplastic structure. The respective portions 17, 19 may be secured by thermo-welding along a parting line 15, or alternatively, by pressure thermo-welding along a parting line 15. The core foam 16, while fluid, is pressure-injected into the sealed structure of the top and bottom portions 17, 19 to adhere to the interior of each of the portions 17, 19.

The interior side of the top portion 17 and interior side of the bottom portion 19 are corrugated or rough textured in such a manner that when the foam 16 is injected, the bond of the foam 16 interlocks to the interior side of the top portion 17 and to the interior side of the bottom portion 19, thereby minimizing delamination. Foam 16 completely fills the interior of the board 10 and bonds exceptionally well to the corrugated or rough textured interior surfaces.

Figure 7:
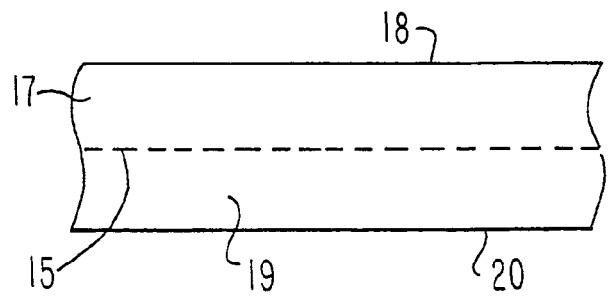
FIG. 7 is a partial side view of a portion of the board, showing joiner between opposed portions of the board by thermoplastic welding of the thermoplastic material.

As shown within FIG. 7, the parting line 15 for the respective top and bottom portions 17, 19 may lie about at the middle of the thickness of the board 10 defined by the side surfaces 22, 24, thus to define "halves", although the precise location of the parting line may vary. Therefore, the portions 17, 19 are alternatively referred to as top half or top portion, and bottom half or bottom portion. After the foam has been injected into the interior of the thus-formed structure, the unitary, foam-filled, structure is completed.

The board 10 is sealed as described to prevent passage of blood-borne pathogens from residing in the interior of the board 10, or from re-use of the board, so that a risk of transmission of disease from a first user to a second user, or to firefighters, or EMS personnel using the board, is minimized. In effect, such pathogens have no migration path to an interior surface to rest and multiply. Therefore, a risk of passing infectious diseases inherited from a first use of the board 10 inadvertently to a second use of the board 10 is minimized.

The spine board 10 thus structured is further characterized by its ease of use, and buoyancy in water for aquatic emergencies. A feature of the board 10 is that it is stable, substantially symmetrical along a longitudinal axis 25, shown in FIGS. 1, 2, 5A, 5B, 6A and 6B, and sufficiently rigid (as will be further explained) to permit usage with a maximum human weight consistent with strap maximums. A further discussion of strength-inducing features is set forth in connection with the specific structure of the spine board 10.

The spine board 10 is free from metal parts as structured. Therefore, when used with non-metal straps to hold an emergency patient secured to the board 10, such as straps secured by hook and loop fasteners (i.e., VELCRO brand fasteners or their equivalent), the patient need not be moved for diagnosis. The feature that the spine board 10 is X-ray translucent and/or radio translucent is a time-saving feature particularly useful in emergency situations where seconds may be critical to saving a patient's life, or to alleviate further damage by permitting immobile diagnosis with a minimum of movement.

Returning to the structure as shown in FIG. 1, the spine board 10 has a plurality of side hand holds 27, respectively identified by the reference numbers 27a, 27b, 27c, and 27d to refer to the right side hand holds, and the reference numbers 27e, 27f, 27g, and 27h to refer to the left side hand holds. Each hand hold 27 is similarly structured with a curved head end arch 27i and a curved tail end arch 27j, merging into an interior side wall 27k, and an exterior side wall 27m (the letter l having been ignored because of its appearance similar to the number 1). The side walls 27a to 27m thus are located through the entire thickness of the board, are sealed, and thus define openings sized to received the hands of a board handler when toting the board with a patient attached. The longitudinal lengths of the side walls 27k and 27m may vary, so long as ease of use, particularly with a gloved hand, is respected. As shown, the hand holds 27a and 27e nearest the head end 12 is longer than the three other hand holds 27b, 27c, 27d, 27f, 27g, and 27h along the sides of the board 10.

A result of this hand hold structure having sealed openings 27 penetrating the thickness of the spine board 10, is also to strengthen the board, while reducing its overall weight. In summary, the side hand holds 27 are sized to accommodate comfortably and conveniently the gloved hands of emergency personnel.

Another significant feature of the side hand holds 27 will be discussed. Each side hand hold 27 has at least one pin 30 molded between the interior side wall surface 27k and the exterior side wall surface 27m. The pin 30 is formed at the same time that the top portion 17 or the bottom portion 19 to be integral therewith, without access from the exterior of the spine board 10 to its foam filled interior. Preferably, the hand holds 27a, and 27e have two pins 30, while the other hand holds 27b, 27c, 27d, 27f, 27g, and 27h have one pin 30. This structure, thus, maintains the sealed character of the spine board 10 as previously discussed.

The pins are sized to receive a speed clip on safety straps (not shown) to be attached to the pins 30. Conventionally, such speed clip pins as are currently used are about one quarter of an inch in diameter, so that the pins 30 are of a like range of sizes. Each pin 30 is generally shaped like a barbell, having areas of greater diameter nearest to the interior and exterior side walls 27k and 27m, and a narrower diameter at about the middle of that length between those walls. This diameter variation causes the speed clip to center naturally on the narrowest diameter portion of the pin 30 and, thus, seat itself primarily at that location.

It may be again noted that the side hand holds 27a, 27e nearest to the head end and most remote from the tail end 14 each have two pins 30. Thus, as shown, for a spine board having about a 6 foot length, five locations for the pin 30 are shown. This number may be greater or lesser so long as flexibility in the number and location of the pins 30 is provided. This feature accommodates adult heights as contrasted to children heights, and a normal range of heights for adults. Thus, a child of an exemplary height of 30 inches can be strapped by selecting pins spaced for straps clipped to such pins at about the child's chest and thighs. Similarly, different, longitudinally spaced pins for straps placed at about an adult's chest and thighs can accommodate the adult of an exemplary height of 6 feet. The plurality of pins 30 is thus responsive to possible height variations in the distressed patient who is using the spine board 10. This flexible feature is another example in which the spine board 10 may be used during an emergency without losing precious seconds to accommodate varying patient heights.

The arch shapes of the head end arches 27i and the tail end arches 27k have been noted. It is a feature of the invention to use rounded edges on the vacuum-formed moldings to assure completely filled interior structures. It is also a feature of the hand holds 27 that their glove-receiving surfaces 72 and/or pins 30 may electively be roughened or mottled to provide a greater non-slip surface for the gripping surfaces of the hand holds 27.

Figure 4:
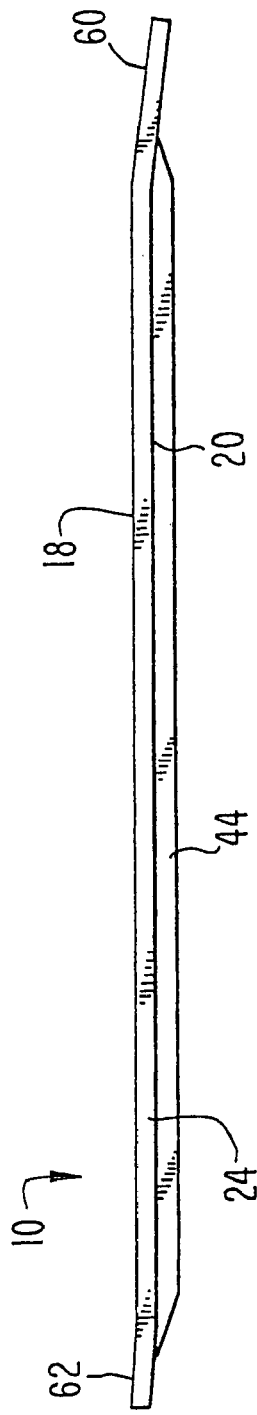
FIG. 4 is a right side view of an embodiment of the invention, with the left side view being substantially the same.
Figure 5A:
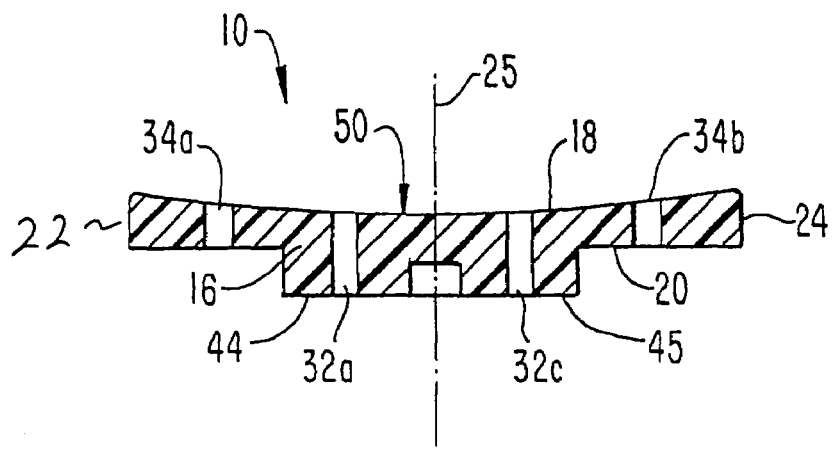
FIGS. 5A and 5B are cross sectional views taken along line 5-5 of FIG. 2, showing a cradle structure for the top surface of the board and representing a foam interior for the board.
Figure 6A:
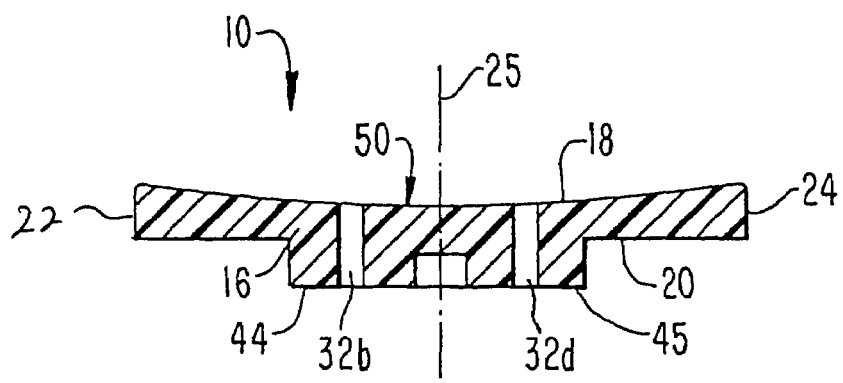
FIGS. 6A and 6B are cross sectional views taken along line 6-6 of FIG. 2 showing the cradle structure and risers on the bottom of the board, having a height about equal to the distance between the tail end of the board and the bottom surface.
Figure 5B:
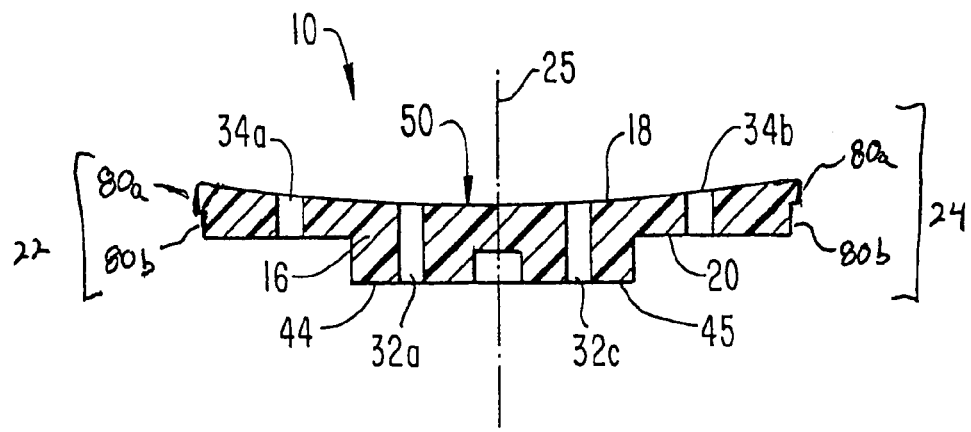
Figure 6B:
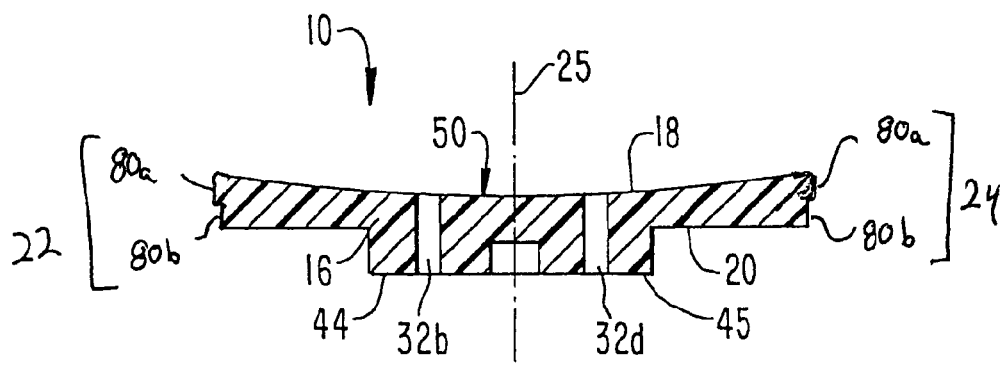

FIGS. 5A and 5B are cross sectional views taken along line 5-5 of FIG. 2, while FIGS. 6A and 6B are cross sectional views taken along line 6-6 of FIG. 2. The cross sections of FIGS. 5A, 5b, 6A and 6B are transverse to the view of FIG. 4. These cross sections depict a deck cradle 50 in the top surface 18 of the spine board 10, risers 44, 45 on the bottom of the spine board 10, and side walls 22, 24 at the peripheral edges of the spine board 10.

The deck cradle 50 is for housing the patient using the board 10. This deck cradle 50 is smooth for additional comfort in positioning the patient fore and aft and, to a more limited extent, side to side, prior to securing the patient with a flexible strap. The deck cradle 50 further includes a generally planar area to accommodate a label, identifying the board 10 with its manufacturer, seller, or owner of the board, for example.

Risers 44, 45 have a height about equal to the distance between the tail end 14 of the board and the bottom surface 20.

FIGS. 5A and 6A depict side walls 22, 24 on the peripheral edges of the spine board 10 without a flange configuration. Alternatively, FIGS. 5B and 6B depict side walls 22, 24 on the peripheral edges of the spine board 10 having a flange configuration that includes flange 80a protruding from a surface portion 80b of side walls 22, 24 to provide the edge of the spine board 10 additional grip.

The spine board 10 also includes a plurality of longitudinally-oriented longitudinal submersion-assisting slots 32a to 32d. Slot 32a is spaced apart from slot 32c longitudinally and relative to the center line 25 of the spine board 10. Slot 32b is spaced apart from slot 32d also longitudinally and relative to the center line 25 of the spine board 10. Such slots 32a to 32d define openings through the thickness of the board 10 to assist in rapid submersion during aquatic rescues, by providing a fluid flow through path. These slots 32a to 32d, together with the side holds 27 also lessen the weight of the board 10, assist its submersibility in water, and by being spaced longitudinally do not diminish the strength of the foam-filled board against flexing. It is a feature of the invention to maintain stability against bowing or flexing of the board 10 around potential axes orthogonal to the main longitudinal axis 25.

A pair of openings 34a, 34b are defined in the board 10 at spaced locations wider than the locations between the slots 32a to 32d. These openings 34a, 34b have accommodate straps of a head immobilizer of a type currently known and used in the art.

A pair of head end hand holds are defined by openings 36a, 36b are located near the head end 12 of the board 10 at spaced apart locations opposite each other relative to the longitudinal axis of the board 10. These hand holds 36a, 36b are spaced apart at the relatively wider, head end 12 of the board 10 and are sized to accommodate a grip of a person who primarily walks backwards while holding the board 10 with its secured patient thereon when moving a patient toward an emergency vehicle, for example. In contrast, a person lifting at the tail end 14 of the board generally walks forward while moving the board in a direction toward the head end 12. It is also a feature of the hand holds 36a, 36b that their glove-receiving surfaces 72 may electively be roughened or mottled to provide a greater non-slip surface for the gripping surfaces of the hand holds 36a, 36b.

A pair of adaptor openings 38a, 38b are located intermediate the head end hand holds 36a, 36b located about on the longitudinal axis 25. These adaptor openings 38a, 38b are sized and located to accommodate another conventional head immobilizer, different from the one previously discussed.

Finally, a pair of tail end hand holds 40a, 40b are provided at the tail end 14 of the board 10. The hand holds 40a, 40b are defined by openings passing through the entire thickness of the foam-filled spine board 10, and are at a inwardly turned angle as compared with the side hand holds 27 previously discussed. This location, generally parallel to the inwardly turned side walls 22, 24 respectively, accommodates outwardly turned gloved hands, grasping the hand holds 40a, 40b from outside the side walls 22, 24 of the board 10. This is in contrast to the hand holds 36a, 36b at the head end 12 of the board 10, intended to be grasped by a gloved hand from beneath the board in a direction parallel to the front end, as in a "curl" position. It is also a feature of the hand holds 40a, 40b that their glove-receiving surfaces 72 may electively be roughened or mottled to provide a greater non-slip surface for the gripping surfaces of the hand holds 40a, 40b.

Turning now to the bottom view of the board shown in FIG. 3, it will be noted that a generally C-shaped structure 42 is shown having a first portion 43 extending transverse to the board and a pair of spaced, generally longitudinally extending risers 44, 45 upraised slightly relative to the bottom surface of the main body 13 as seen in the side view of FIG. 4, thus to define upraised board rests or ribs on which the board 10 rests when positioned on the ground. This feature thus permits a quicker grasping of the board 10 during use. As seen from FIG. 1 and the side view of FIG. 4, these ribs extend downwardly a distance greater than the vertical distance of the distal end of the tail end 14 of the board. It is noted that the tail end 14 terminates a downwardly extending tail portion 60, extending from about the location of the ends of the risers 44, 45 of the C-shaped portion 42, while the head end 12 has a slightly upraised portion 62, slanting upwardly a slight distance from about the portion 43 of the C-shaped portion 42.

The fore and aft upwardly extending and downwardly extending portions provide comfort to a patient secured to the board 10 and are best seen in FIG. 4.

The colors of the plastic for the board 10 may vary, but the bright lime green color, or a luminescent color may prove most effective, and eye-catching. Bold colors for the board 10 make it easier to locate under stressful, perhaps smoky or darkened locations from its usual storage location on an emergency vehicle, such as a fire truck, or ambulance.

To inhibit scratching of the tail end 14, the spine board 10 may include a coating on the tail end 14. Polystyrene, or the like, being applied to the tail end 14 as the coating is within the scope of the present invention.

FIG. 8 shows a representative flow chart of the steps for manufacturing the board of the type described in connection with FIGS. 1 to 7. In a step S1, one half or portion of the board 10 is vacuum formed from a thermoplastic material in a mold having a complementary structure to produce a half of the board 10 shown in FIGS. 1 to 4. In a step S2, the other half or portion of the board 10 is vacuum formed from a thermoplastic material in a mold having a complementary structure to produce another half or portion of the board 10 shown in FIGS. 1 to 4. The thermoplastic material is preferably an ABS resin having a strength sufficient to accept an infusion of foam without deformation because it is placed in a secondary mold fixture that allows over-packing the foam without deformation. Thereby, a void-free and stronger foam cord spine board is attained. The steps S1 and S2 may be carried out serially, or simultaneously.

In a step S3, the one half or portion is adhered to the bottom half or portion to form a hollow unitary board structure having at least two openings for injecting foam into the interior of the unitary board structure for reasons that will become apparent.

Figure 9:
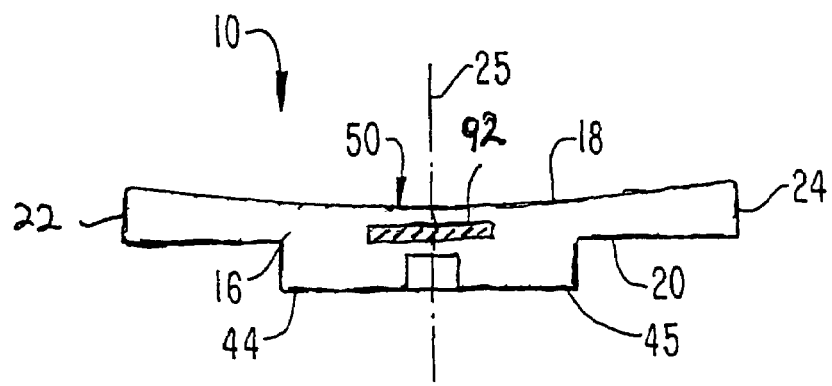
FIG. 9 is a cross sectional view showing a radio chip within the hollow unitary board structure.

As shown within FIG. 9, disposing a radio chip 92 within the hollow unitary board structure during step S3 is also within the scope of the present invention. When interrogated by a signal originating from a signal source external to the unitary board structure, the radio chip 92 will transmit a signal for identifying the spine board 10.

In a step S5, urethane foam or an equivalent having a specific gravity after insertion of less than 1.00 is blown into the interior of the unitary board structure through at least one opening, another of the openings serve to permit the expulsion of air from the interior of the unitary board structure as the unitary board structure fills with foam. After the unitary board structure is full of foam, and air pockets removed, the openings for an ingress of the foam and egress of the air are sealed, as in a step S6, so that the unitary board structure with the foam therein form a sealed unitary board structure with foam in its interior.

The urethane foam adheres to the interior walls of the unitary board structure, thus to form a board 10 that is resistance to bending laterally or longitudinally under loads of the type contemplated by the end use and the limitations of the flexible straps, as discussed above. It is contemplated that the vacuum forming of the respective complementary portions, i.e. the top half or portion and the bottom half or portion, will produce a structure having the side hand holds 17, the head end hand holds 27a, 27e, the tail end hand holds 40a, 40b, and the respective other openings unitarily formed therein in register, so that when the two portions are adhered, such as by pressure thermo-welding, or by heat welding, the through holes, or risers and ridges described hereinabove are formed sufficiently to seal the interior of the structure from access by invasive pathogens.

The preference for curved and or rounded corners in both a lateral and longitudinal direction has been previously mentioned. When so structured, the interior of the unitary board more readily receives the foam without leaving air pockets therein. The net result preferably is a foam-filled board having a specific gravity of about 1.00 or so to less that 1.00 and with a buoyancy determined by its displacement in water sufficient to cause the board to float in aquatic conditions.

Thus, a rescue spine board 10 used for immobilization and/or transfer of an injured person resulting from accidents or trauma has been described. The spine board 10 is particularly useful in immobilizing persons suspected by a firefighter or EMS technician of suffering from spinal injuries. The board 10 includes a number of features relating to firefighter, EMS or aquatic situations, minimizing the rescuer time at the "scene" of the accident, injury, trauma or sudden illness.

Practically, the board contemplated has length of about 6 feet, with a head end width of about 16 inches and a tail end width of about 12 inches. The space for the decal or log is about 16 inches longitudinally and about 5 inches laterally.

Among those design features as previously discussed are:

1. The board 10 is easy to use, with no moving parts other than the flexible belt to be secured to pins in the side hand holds to extend about the torso of a patient.

2. The board 10 is sealed and thus resistant to retention of blood-borne pathogens.

3. The board 10 meets requirements of firefighters, EMS technicians, and other emergency individuals.

4. The board 10 is stable while loaded, with a rigidity and strength to maximize performance.

5. The board 10 is X-ray translucent and/or radio translucent when used with flexible straps having no metal parts.

6. The board 10 is designed to accommodate two diverse currently-available head immobilizers.

7. The sizes of the respective hand holds permit greater vertical strap adjustments and safety glove clearance.

8. The dropped tail feature allows for spine board placement under a person in a seated-like position such as in a car, truck, heavy equipment, or other type space. Once placed under the person, the angle of extrication is a more horizontal angle of departure. This in turn, minimizes the amount of energy to move the person onto the spine board from the scene for transport and allow for a better lifting technique. Thus, minimizing the likelihood of additional injuries to the injured person or to the firefighters, EMS personnel, rescuers, or bystanders assisting in the extrication.

9. With its risers, the board 10 is easy to grasp when flat on the ground or pool edge.

10. The hand holds of the board are textured to accommodate wet rescue, and the pins are formed from the same thermoplastic material.

11. The deck cradle is smooth and contoured to accommodate a patient comfortably, for longer periods of time.

12. Other advantages and features, such as those relating to log space, coloring, and the like are stated in the specification.

These and other features of the invention may be modified within the scope of the appended claims. The descriptions and drawings herein are presented to facilitate an understanding of the present invention, and not to limit the scope of the present invention that is claimed below.

What is claimed is:

1. A method of making a spine board, comprising:
   forming each of a pair of mating board portions together defining said board that includes at least one speed clip attachment site having an integral molded pin made from the same material as said board for receiving quick-connecting clips when strapping a patient to the spine board;
   thermo-welding one of said pair to another of said pair to define a hollow unitary board structure incorporating said integral molded pin at said speed clip attachment site;
   then injecting foam into the interior of said unitary board structure through in ingress opening, while providing egress for air from said interior, until said foam fills said interior completely and adheres to the interior of each of said pair of mating board portions, and
   sealing said ingress opening after said foam has completely filled the interior of said board sufficiently to prevent a migration path for fluids to an interior of said spine board including at said speed clip attachment site.

2. The method as set forth in claim 1, wherein the step of forming is a single step of vacuum forming a thermoplastic material.

3. The method as set forth in claim 1, wherein, in the step of injecting foam, wherein said foam adheres to the interior of said unitary board structure, said unitary board structure being corrugated or rough textured to accept the foam, thereby avoiding delaminating of the structure itself.

4. The method as set forth in claim 1, further including a step of positioning said unitary board structure in a secondary mold prior to injecting said foam.

5. The method as set forth in claim 1, wherein said foam is urethane foam.

6. The method as set forth in claim 1, wherein said integral molded pin is barbell-shaped to center the speed clip at a center of the pin.

7. The method as set forth in claim 1, wherein said integral molded pin is located between opposed side walls of a hand-hold in said board.

8. The method as set forth in claim 1, wherein said each of said pair of mating portions includes a downwardly turned tail portion to allow placement of said spine board under a person so that an angle of extrication presents a horizontal angle of departure of that person.

9. A method of making a spine board from a thermoplastic material, comprising:
   forming each of a pair of mating board portions from said thermoplastic material together defining said board that includes a plurality of speed clip attachment sites, each having an integral molded pin made from the same material as said board for receiving quick-connecting clips when strapping a patent to the spine board;
   thermo-welding one of said pair to another of said pair to define a hollow unitary board structure incorporating said integral molded pin at said speed clip attachment site;
   then, injecting foam into the interior of said unitary board structure through in ingress opening, while providing egress for air from said interior, until said foam fills said interior completely and adheres to the interior of each of said pair of mating board portions, and
   sealing said ingress opening after said foam has completely filled the interior of said board to prevent a migration path to the interior of said board for fluids, including at said speed clip attachment sites.

10. The method as set forth in claim 9, wherein the step of forming is a single step of vacuum forming a thermoplastic material.

11. The method as set forth in claim 10, wherein said foam is urethane foam.

12. The method as set forth in claim 9, wherein, in the step of injecting foam, said foam adheres to the interior of said unitary board structure, said unitary board structure being corrugated or rough textured to accept the foam, thereby avoiding delaminating of the structure itself.

13. The method as set forth in claim 9, further including of positioning said unitary board structure in a secondary mold prior to injecting said foam.

14. The method as set forth in claim 9, wherein said integral molded pin is barbell-shaped to center the speed clip at a center of the pin.

15. The method as set forth in claim 9 wherein said integral molded pin is located between opposed side walls of a hand-hold in said board.

16. The method as set forth in claim 9, wherein said each of said pair of mating portions includes a downwardly turned tail portion to allow placement of said spine board under a person so that an angle of extrication presents a horizontal angle of departure of that person.

17. A method of making a spine board, comprising:
   forming each of a pair of mating board portions, each made from a thermoplastic material, together defining said board, each of said top and bottom board portions having an interior side that interlocks with foam injected into said spine board to minimize delamination, said spine board including at least one speed clip attachment site having an integrally molded pin of the same thermoplastic material;
   thermoplastic welding one of said pair to another of said pair to define a sealed, hollow unitary board structure;
   securing said unitary board structure within a secondary mold;
   injecting foam into the interior of said unitary board structure secured in said secondary mold through an ingress opening, while providing egress for air from said interior, until said foam completely fills and adheres to said interior of said board portions, and
   sealing said ingress opening after said foam has completely filled the interior of said board to form a unitary sealed structure having no path for fluids from an exterior of said structure to the interior of said structure, including at speed clip attachment sites.

18. The method as set forth in claim 17, wherein the step of forming is a single step of vacuum forming a thermoplastic material.

19. The method as set forth in claim 17, wherein, in the step of injecting foam, said foam adheres to the interior of said unitary board structure, said unitary board structure being corrugated or rough textured to accept the foam, thereby avoiding delaminating of the structure itself.

20. The method as set forth in claim 17, further including of positioning said unitary board structure in a secondary mold prior to injecting said foam.

21. The method as set forth in claim 17, wherein said foam is urethane foam.

22. The method as set forth in claim 17, wherein said integral molded pin is barbell-shaped to center the speed clip at a center of the pin.

23. The method as set forth in claim 17, wherein said integral molded pin is located between opposed side walls of a hand-hold in said board.

24. The method as set forth in claim 17, wherein said each of said pair of mating portions includes a downwardly turned tail portion to allow placement of said spine board under a person so that an angle of extrication presents a horizontal angle of departure of that person.

* * * * *